(12) United States Patent
Touchet et al.

(10) Patent No.: US 10,743,922 B1
(45) Date of Patent: Aug. 18, 2020

(54) VARIABLE ANGLE LOCKING CONSTRUCT FOR ORTHOPEDIC APPLICATIONS

(71) Applicant: Trilliant Surgical LLC, Houston, TX (US)

(72) Inventors: Tyler Touchet, Cypress, TX (US); Christopher Radzicki, Cypress, TX (US)

(73) Assignee: Trilliant Surgical LLC, Houston, TX (US)

( * ) Notice: Subject to any disclaimer, the term of this patent is extended or adjusted under 35 U.S.C. 154(b) by 0 days.

(21) Appl. No.: 16/585,762

(22) Filed: Sep. 27, 2019

(51) Int. Cl.
*A61B 17/80* (2006.01)
*A61B 17/86* (2006.01)

(52) U.S. Cl.
CPC ...... *A61B 17/8052* (2013.01); *A61B 17/8605* (2013.01)

(58) Field of Classification Search
CPC ................................................ A61B 17/8052
See application file for complete search history.

(56) References Cited

U.S. PATENT DOCUMENTS

| 8,105,367 B2 | 1/2012 | Austin et al. |
| 8,906,076 B2 | 12/2014 | Mocanu et al. |
| 10,258,395 B2 * | 4/2019 | Pak .................... A61B 17/8047 |

OTHER PUBLICATIONS

Wikipedia, "Countersink," accessed Sep. 24, 2019, 4 pages total, URL: https://en.wikipedia.org/wiki/Countersink.
Wikipedia, "Counterbore," accessed Sep. 24, 2019, 3 pages total, URL: https://en.wikipedia.org/wiki/Counterbore.

* cited by examiner

*Primary Examiner* — Andrew Yang
(74) *Attorney, Agent, or Firm* — Trop, Pruner & Hu, P.C.

(57) ABSTRACT

An embodiment includes a bone fixation system comprising: a bone anchor with a tapered head, the head being threaded; and a plate that includes a void, the void including one of a counterbore or a countersink; wherein: (a) no portion of the void is threaded; (b) the void includes an inner wall; (c) the inner wall includes reliefs along its perimeter. Other embodiments are described herein.

23 Claims, 5 Drawing Sheets

VARIABLE ANGLE LOCKING CONSTRUCT FOR ORTHOPEDIC APPLICATIONS

TECHNICAL FIELD

Embodiments of the invention are in the field of orthopedic applications.

BACKGROUND

It is common practice in orthopedics to drive bone screws into bone via holes in a fixation plate. This allows for the stabilization of osteotomies, fractures, bone fragments, and the like. Often a user may desire for a screw to lock to the plate to prevent the screw from backing out from the plate after insertion of the screw into bone. The desired angle at which a locked screw engages a hole in the plate may vary from normal to the central axis of the hole depending on patient anatomy or additional hardware.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. For example, not every portion of a device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Phrases such as "comprising at least one of A and B" include situations with A, B, or A and B.

An embodiment includes a variable angle locking screw and plate system that does not require the plate include a threaded or tapered hole. Locking the screw to the plate allows for the biomechanical load to be transferred from the screw to the plate in a more efficient manner than would be the case with standard non-locking screw/plate systems. The load transfer may aid in the healing process as the reduction of, for example, the osteotomy or fracture is maintained.

Figure 2A:
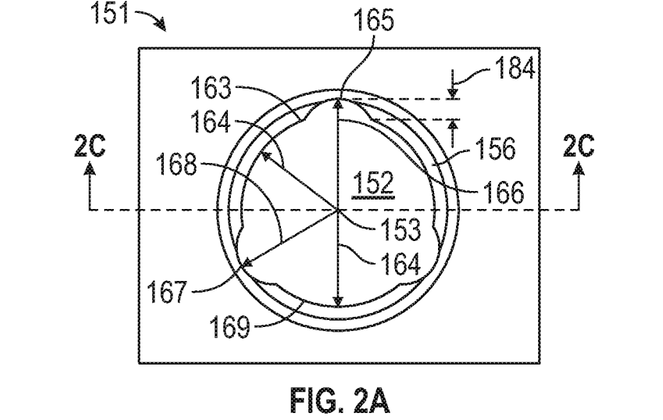
FIGS. 2A, 2B, 2C include a top view, a perspective view, and a cross-sectional view of a bone plate in an embodiment.

An embodiment includes a bone fixation system comprising a bone anchor 101 and a plate 151. While the plate in FIG. 2A shows a single aperture, this is for clarity and embodiments may include 1, 2, 3, 4, 5, 6 or more holes.

Figure 1:
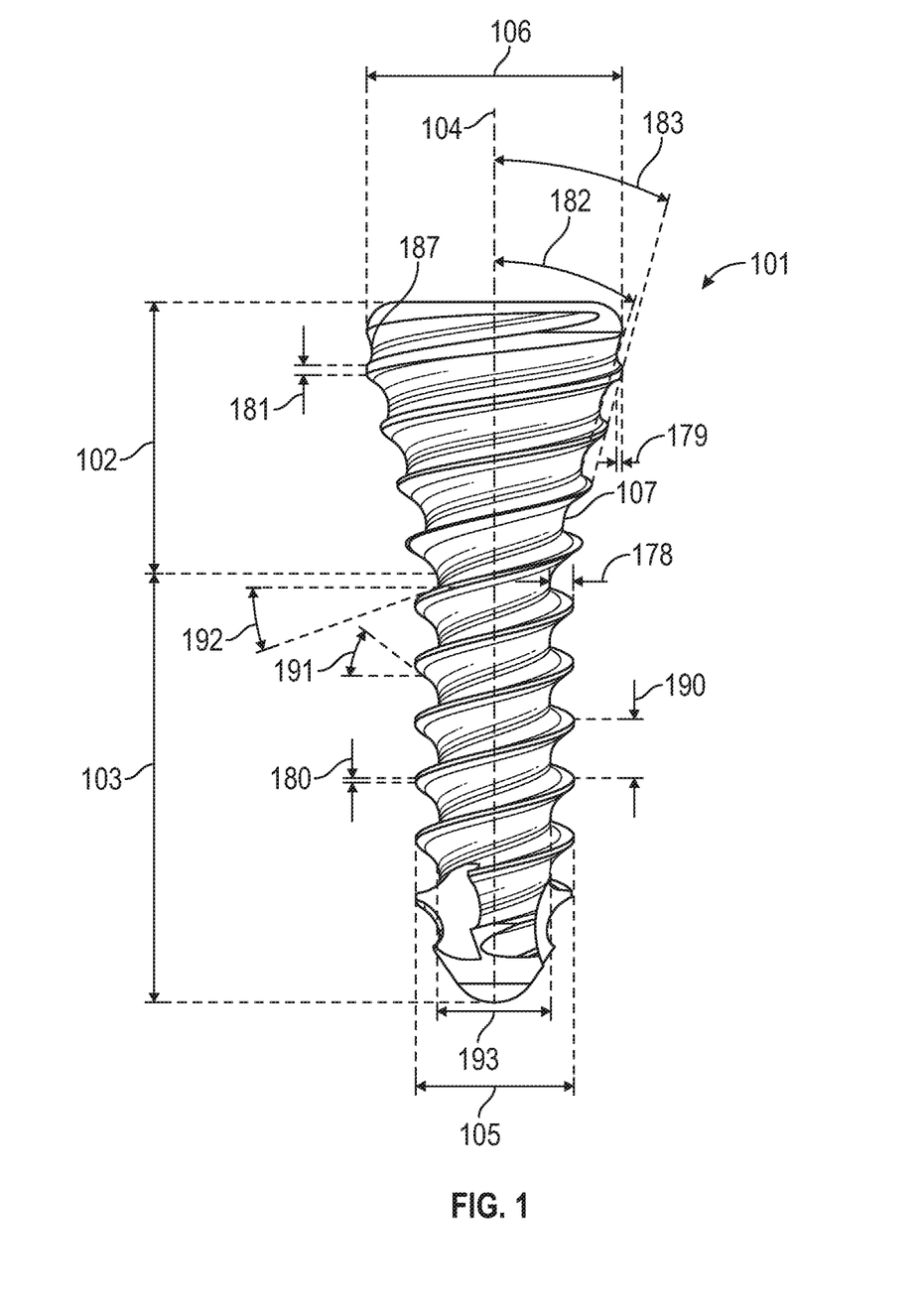
FIG. 1 includes a bone anchor in an embodiment.

The bone anchor includes a head 102, a body 103, and a long axis 104. The body has an outer diameter 105 that is orthogonal to the long axis and the head has an outer diameter 106 that is orthogonal to the long axis. While the body is not tapered in FIG. 1 other embodiment may have a tapered body wherein (a) the thread root 107 (where a thread meets the non-threaded portion of the body) may be tapered, (b) the thread crest (outermost edge of thread) may be tapered, (c) thread root and thread crest are both tapered at the same angle of incidence to the long axis, or (d) thread root and thread crest are tapered at different angles of incidence to the long axis. In FIG. 1 the outer diameter of the head diameter 106 is greater than the outer diameter of the body 105.

Figure 2B:
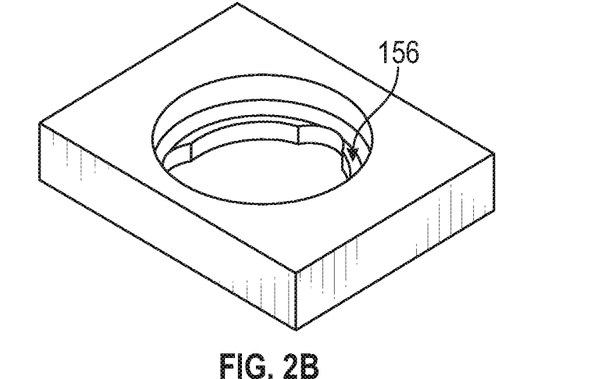
Figure 2C:
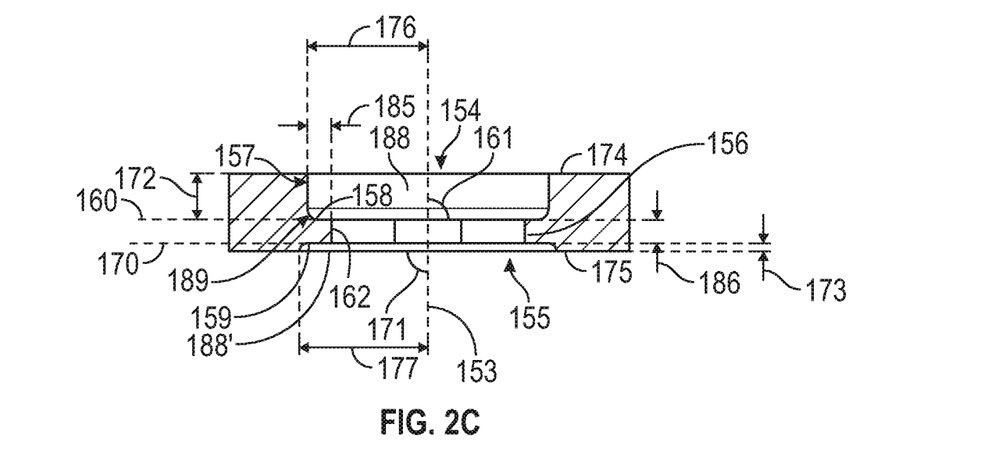

The plate includes an aperture 152 and the aperture includes a long axis 153 that traverses the aperture but does not intersect the plate. The aperture includes a first opening 154 and a second opening 155. The aperture includes a projection 156 and the projection projects inwardly from a wall 157 of the aperture and towards the long axis. The projection has a first surface 158 and a second surface 159. At least a portion of the first surface is coplanar with a first plane 160. The first plane 160 intersects the long axis at a first angle 161 which is 90 degrees. However, in other embodiments the first angle is between 85 degrees and 95 degrees, between 75 degrees and 105 degrees, or between 65 degrees and 115 degrees.

Projection 156 includes an inner wall 162 that couples the first surface of the projection to the second surface of the projection. The inner wall of the projection has a first portion 163 that is a first distance 164 from the long axis 153, the first distance being orthogonal to the long axis. The inner wall of the projection has a second portion 165 that is a second distance 166 from the long axis, the second distance being orthogonal to the long axis. The second distance is greater than the first distance due to portion 165 being in a void, recess, or relief formed along the wall 162. In an embodiment the inner wall of the projection has a third portion 167 that is a third distance 168 from the long axis, the third distance being orthogonal to the long axis. The third distance is greater than the first distance.

In an embodiment the third distance 168 is greater than the second distance 166 (not shown in FIG. 2A). Thus, reliefs may be formed at varying depths that are unequal to each other. The second distance is measured from a location of the second portion that is furthest from the long axis as compared to other locations of the second portion (i.e., the deepest portion of the relief) and the third distance is measured from a location of the third portion that is furthest from the long axis as compared to other locations of the third portion.

In an embodiment the inner wall of the projection defines an inner perimeter of the projection. The inner wall of the projection has a fourth portion 169 that is the first distance 164 from the long axis.

In an embodiment distance 166 is between 0.508 mm and 1.016 mm and is greater than distance 164 by a differential distance 184 and the differential distance is between 0.127 mm and 0.381 mm.

In an embodiment at least a portion of the second surface is coplanar with a second plane 170. The second plane intersects the long axis at a second angle 171 which is 90 degrees. However, in other embodiments the second angle is between 85 degrees and 95 degrees, between 75 degrees and 105 degrees, or between 65 degrees and 115 degrees.

In FIG. 2C the first surface 158 is a first distance 172 from the first opening, the first distance being parallel to the long axis. The second surface is a second distance 173 from the second opening, the second distance being parallel to the long axis. The first distance is greater than the second distance. This may allow greater clearance for the plate to accept a bone anchor to thereby allow a greater angle of insertion of the anchor into the plate. However, in other embodiments these distances may be the same.

In an embodiment distance 173 is between 0.254 mm and 1.27 mm and distance 172 is between 0.254 mm and 5.588 mm. In an embodiment portion 163 of the projection projects inwardly from the wall 157 of the aperture and towards the long axis by distance 185 which is between 0.254 mm and 0.127 mm. In an embodiment thickness 186 is between 1.00 mm to 2.75 mm.

Dimensions as used herein are examples and various embodiment may or may not include such dimensions.

In an embodiment the plate 151 includes no threads between the first and second openings 154, 155. The first opening 154 directly interfaces a first outer surface 174 of the plate; the second opening 155 directly interfaces a second outer surface 175 of the plate; and the first outer surface 174 of the plate opposes the second outer surface 175 of the plate. By avoiding the use of threads, the locking angle can be increased without shearing the projection material off or creating burrs. Additionally, once a screw is locked in a threaded construct at an angle, the threads are damaged and relocking at different angles may be difficult. Avoiding threads allows for high angulation and repeated locks. Additionally, one is not limited by just one screw design or thread profile, unlike many other conventional locking constructs.

In an embodiment the first opening has a first maximum diameter (twice radius 176 in the example of FIG. 2C) that is orthogonal to the long axis and the second opening has a second maximum diameter (twice radius 177 in the example of FIG. 2C) that is orthogonal to the long axis. In an embodiment the second maximum diameter is greater than the first maximum diameter but in other embodiments the two diameters may be equal or the first diameter may be greater than the second diameter.

Figure 3A:
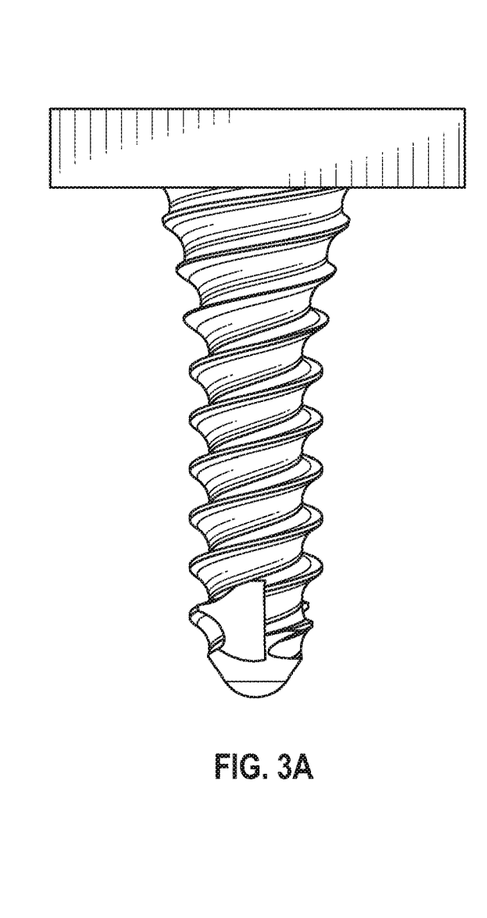
FIGS. 3A, 3B, 3C include a side view, a cross-sectional view, and a top view of a bone plate in an embodiment.
Figure 3B:
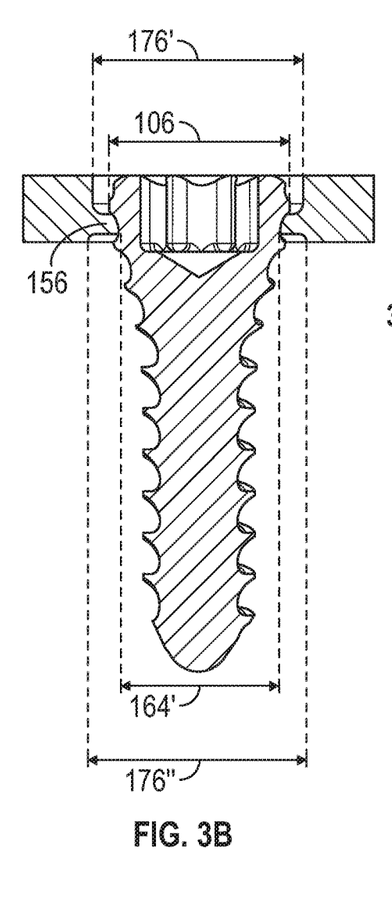

In FIG. 3B the head 102 of the bone anchor includes a maximum diameter 106. Plate opening 154 maximum diameter 176' is greater than the maximum diameter 106. Also, projection 156 forms a ring that circumnavigates an inner portion of the aperture. The ring has a minimum diameter 164' that is less than the maximum diameter 106. As used herein, a "maximum" diameter may accommodate situations where, for example, a surface is not circular. For example, opening 154 may be non-circular in some embodiments and therefore include more than one diameter such that the "maximum" diameter is the largest of the multiple diameters.

In an embodiment the maximum diameter 106 of the head of the bone anchor is between 5 percent and 10 percent larger than the minimum diameter 164' of the ring.

In FIG. 1 at least a portion of the head 102 of the bone anchor is included in a proximal-most fifth (20 percent) of the bone anchor and the portion includes threads. In other words, at least a portion of the bone anchor head is threaded. In FIG. 1 the body 103 of the bone anchor includes threads. The threads of the body of the bone anchor have a first thread height 178 and the threads of the portion of the head of the bone anchor have a second thread 179 that is less than the first thread height.

In FIG. 1 the threads of the body of the bone anchor have a first crest width 180 and the threads of the portion of the head of the bone anchor have a second crest width 181 that is greater than the first crest width. However, in other embodiments the widths 180, 181 are equal to each other and in still other embodiments width 181 that is less than width 180.

In FIG. 1 thread height 179 is between 0.0254 mm and 0.3048 mm and crest width 181 is between 0.0508 mm and 0.3048 mm.

Figure 3C:
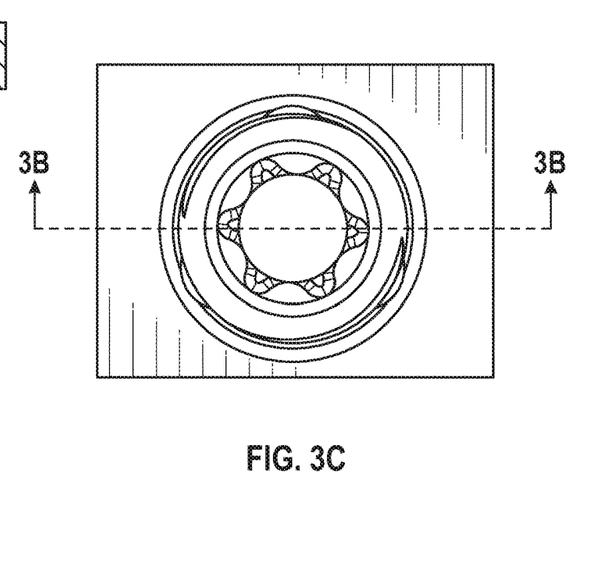
Figure 4A:
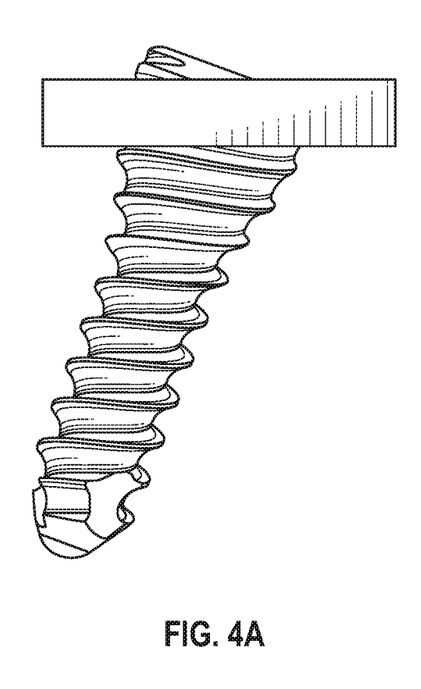
FIGS. 4A, 4B, 4C include a side view, a cross-sectional view, and a top view of a bone plate in an embodiment.
Figure 4B:
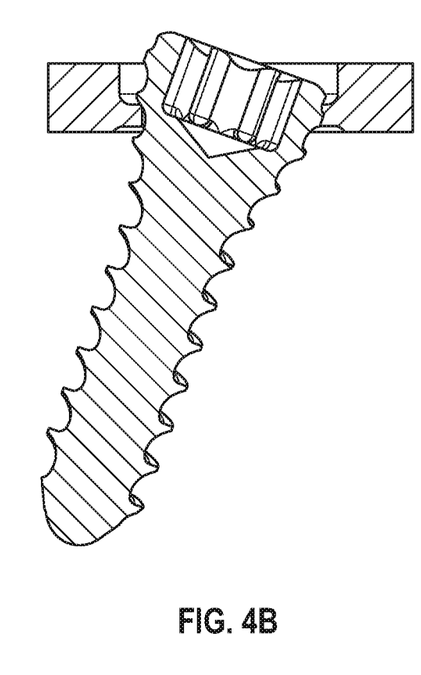
Figure 4C:
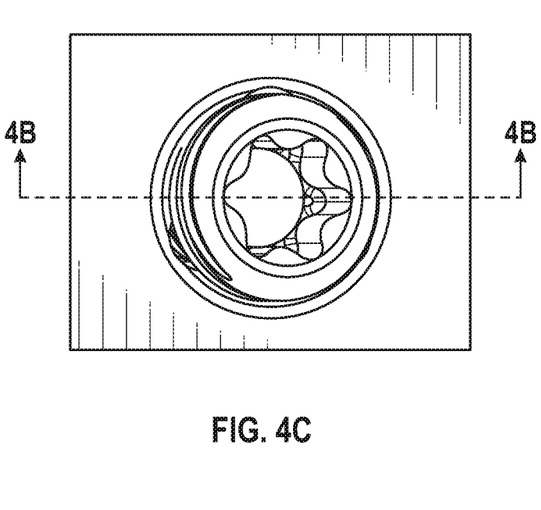

In FIGS. 1, 3C, and 4C the head of the bone anchor has a circular cross-section, the cross-section being orthogonal to the long axis of the bone anchor; and the outer diameter of the head is greater than the outer diameter of the body based on the bone anchor including a tapered portion. The tapered portion includes a thread root that tapers outwardly at an angle 182 between 10 degrees and 20 degrees. The threads of the portion of the head of the bone anchor include thread crests that taper outwardly at an angle 183 between 10 degrees and 20 degrees. However, in other embodiments the tapered portion includes a thread root that tapers outwardly at an angle 182 between 10 degrees and 25 degrees and the threads of the portion of the head of the bone anchor include thread crests that taper outwardly at an angle 183 between 10 degrees and 25 degrees.

An embodiment provides a variable angle locking construct for orthopedic applications by allowing for interference between the locking screw and the screw hole. In an embodiment the locking screw is a dual lead locking screw with a tapered diameter that (measured from one or more thread crests) extends 2.2 mm to 3.5 mm. However, in other embodiments the locking screw is a dual lead locking screw with a tapered diameter that (measured from one or more thread crests) extends 1.6 mm to 7.0 mm. In an embodiment the threaded portion extends throughout the length of the screw. The minor of the screw head is tapered by 12 degrees to 17 degrees and from 8 percent to 80 percent of the total screw length. The major of the screw head is tapered by 7 degrees to 15 degrees but not for the entirety of the head. The proximal portion of the screw head major is not tapered for 5 percent to 15 percent of the screw head. The screw has a minor diameter at the thread breakout 187 ranging from 6 percent smaller to 3 percent larger than diameter 164'. However, in another embodiment the screw has a minor diameter at the thread breakout 187 ranging from 10 percent smaller to 5 percent larger than diameter 164'.

In an embodiment the diameter of the locking threads on the anchor head range from 1 percent to 15 percent larger than diameter 164'. The difference in diameters provides interference with the projection 156 to cause deformation to the aperture at the relief cuts of portions 165, 167 (and any other relief cuts or portions in projection 156).

In an embodiment the anchor contains a diameter 106 that allows for limited interference with the top surface 174 under angulated locking up to 30 degrees from axis 104. However, in another embodiment the anchor contains a diameter 106 that allows for limited interference with the top surface 174 under angulated locking up to 50 degrees from axis 104.

In an embodiment space 188 is formed as a counterbore with a diameter 176' 15 percent to 35 percent larger than diameter 164'. The aperture formed by sidewall 162 is coaxial with the counterbore and allows for mating with the locking screw. Diameter 164' provides interference with the tapered head 102 and locking threads of the head. A radius 189 ranging from 0.0508 mm to 0.381 mm may be present at the bottom of the counterbore to aid in the reduction of stress or manufacturability.

The projection 156 includes a thickness 186 that 40 percent to 60 percent less than the lead of the screw 190 (where a lead is the axial advance of a helix or screw during one complete turn (360°) and wherein the lead for a screw thread is the axial travel for a single revolution).

The locking hole may have a plurality of relief cuts (see, e.g., portions 165, 167) that are radially oriented about the aperture. The presence of the cuts (or, more generally, voids) allows for deformation of the land to occur which aids in the interference fit with the screw.

In an embodiment anchor and plate are made of the same material. Such a material may include, for example, Ti-6Al-4V. However, other biocompatible materials may be used in other embodiments and the anchor and plate do not necessarily require the same material.

Embodiments are suitable for locking bone plates and anchors (such as screws) used for foot/ankle treatment. However, other embodiments are suitable for orthopedics or medicine (human or animal) in general including without limitation applications in foot and ankle, spinal, craniofacial, and/or veterinary arenas and the like.

Embodiments provide for a variable angled locking construct that does not use a tapered plate, threaded plate, or channeled plate.

The relief cuts or voids of the plate may include, 1, 2, 3, 4, 5 or more in alternative embodiments. An embodiment has an absence of the bottom side counterbore (e.g., void 188' is missing). Diameter 164' may range, for example, from 1.0 mm to 7.0 mm or more. Likewise, the anchors may vary in diameter 106 from 1.0 mm to 7.0 mm or more. In an embodiment the screw is not fully threaded and possesses a cap at the head of the screw that does not contain threads. In an embodiment the drive feature of the screw can be of any feature that allows for the transmission of torque from a mating member. In an embodiment the threads of the screw could be embodied in a left-handed thread configuration. In an embodiment the number of screw leads can vary from one to four. In an embodiment the screw head could be spherical in shape as opposed to conical in shape.

An embodiment includes a locking mechanism that locks using a mixture of the "cut-in", "point loading thread-in", and "screw head expansion" and mechanism without the use of a countersink, threaded hole, or tapered hole geometry. Compared to conventional technologies using a two-component system for locking, locking mechanisms addressed herein provide a higher degree of angulation without a compromise in the locking strength. Advantages over conventional systems include the ability to lock at angles exceeding 30 degrees in one direction, which results in a locking cone of 60 degrees. However, in other embodiments advantages over conventional systems include the ability to lock at angles exceeding 50 degrees in one direction, which results in a locking cone of 100 degrees. Additionally, an embodiment allows for multiple locking attempts at varying angles (without using additional components such as a bushing or locking cap). Instead, such an embodiment only requires a locking hole and screw of certain geometries to achieve the same result.

An embodiment includes a screw with two or more continuous threads. The screw includes a conical head and a cylindrical body that make up the overall length of the screw 201. Embodiments of a screw may vary in length from 4 mm to 170 mm. In an embodiment the length is between 8 mm to 50 mm.

In an embodiment the screw has a tapered conical head that extends to the cylindrical body of the screw. In the embodiment the screw is generally cylindrical between the tapered head and the tip of the screw.

In an embodiment the diameter of the screw head is a critical dimension. The diameter 106 of the screw head is imperative for interference that allows for the locking of the screw to the plate and which prevents the screw from translating through the hole without "biting" or locking. The diameter 106 of the screw head can vary from 2.4384 mm to 4.572 mm. In the embodiment the head diameter is equal or larger than diameter 164'. In an embodiment the diameter 106 is 7 percent larger than diameter 164'. However, in other embodiments the diameter 106 is 4, 5, 6, 8, 9, 10 percent larger or more than diameter 164'

In an embodiment the thread height 178 (for the threads on the body) ranges from 0.254 mm to 0.762 mm. In an embodiment the height 178 is 0.381 mm. The thread height is identical between the two threads of the embodiment of FIG. 1 but in other embodiments they can be different with one thread having a larger height than the other.

In an embodiment a critical feature is that the thread height 179 at the head of the screw is different from the thread height 178 for the body of the screw. The thread height 179 is between 0.0254 mm and 0.3048 mm. In an embodiment the thread height 179 is 0.1778 mm. The height of the thread 179 in the tapered head 102 allows for ideal locking into the aperture formed by projection 156. If the thread height 179 is too high, the threads may deform and shear from the head of the screw creating an undesired burr of loose body. Conversely, if the thread height 179 is too low, the locking can be comprised by not contributing to a cut in projection 156.

In an embodiment a critical feature is that the minor head angle 182 (i.e., angle that the root of the thread follows). This feature is critical embodiment because it aids in the formation of the thread head geometry. In various embodiments the angle varies from 10 to 20 degrees and extends 80 to 100 percent of the tapered head 102 from the body of the screw 103. However, in other embodiments the angle varies from 10 to 25 degrees and extends 80 to 100 percent of the tapered head 102 from the body of the screw 103. The angle 182 allows for the threads on the head to bite and wedge into the projection 156.

In an embodiment a critical feature is that the major head angle 183 (i.e., angle that the thread crests follows). This feature is critical in an embodiment because it defines the geometry of the threads on the head. In various embodiments the angle may range from 10 to 20 degrees. However, in other embodiments the angle may range from 10 to 25 degrees. In an embodiment angle 183 is between 15 to 17 degrees. In an embodiment this angle is constant throughout the head of the screw. The angle allows for the threads on the head to bite and wedge into projection 156.

In an embodiment the leading flank angle 191 helps to define the thread geometry and is between 30 and 40 degrees (or between 20 and 50 degrees in other embodiments). In an embodiment angle 191 is 35 degrees. In an embodiment the trailing flank angle 192 helps to define the thread geometry and is between 2 and 8 degrees (or between 2 and 30 degrees in other embodiments). In an embodiment angle 192 is 3 degrees. In an embodiment the lead 190 of the screw (i.e., the pitch divided by each unique thread) is between 0.7366 mm and 1.524 mm. In an embodiment the lead is 0.9906 mm. In an embodiment the crest width 180 (or flats at the edge of the threads) on the body of the screw are between 0.0254 mm and 0.1524 mm.

In an embodiment a critical feature is that the crest width 181 on the head of the screw is/are between 0.0508 mm and 0.3048 mm, with a value being 0.2032 mm in an embodiment. This is critical because the crest needs to be small enough to produce enough stress and/or strain on the projection 156 but large enough so that it does not shear and create a loose body.

In an embodiment thread diameter 105 is the maximum diameter of the threads at the body of the screw. In an embodiment the diameters of all unique threads are equal (e.g., if there are two unique threads on the screw the threads are equal to each other). However, in an embodiment the diameters of all unique threads may be different. In an embodiment diameter 105 is about 2.6924 mm.

In an embodiment the shaft diameter 193 (defined by the diameter created by the root of thread for the body of the screw) is equal for all unique threads and may be about 1.8796 mm. However, in other embodiments diameter 193 may be different for different unique threads. In an embodiment the tip of the screw may be rounded or sharp for self-drilling applications. In an embodiment, root 107 of the thread is made up of two or more geometries such as radii (e.g., 0.2032 mm) and a 0.0254 mm flat.

Regarding the plate, in an embodiment a critical feature includes a use of an upper counterbore. As used herein, a counterbore is a cylindrical flat-bottomed hole that enlarges another coaxial hole. The use of the counterbore creates a flat land 158 that the locking screw can engage. The counterbore may have a depth 172 of 0.762 mm but may range in other embodiments from 0.254 mm to 1.27 mm. In alternative embodiments (e.g., FIG. 5B), the upper portion of the counterbore may have a countersink with total included angle greater than 90 degrees from the central axis 153. As used herein, a countersink includes a conical hole cut into a manufactured object. In embodiment, the counterbore radius 189 may or may not be present and allows for manufacturability of the land feature. Such a radius may be, for example, 0.254 mm.

In an embodiment aperture reliefs are a critical component. For example, in FIG. 2A there are three reliefs but in alternative embodiments there may be 1, 2, 4, 5 or more reliefs. The reliefs are oriented radially from the central axis 153 and are comprised of a diameter 166 ranging from 0.508 mm to 1.016 mm that protrudes into projection 156. The reliefs allow for deformation of the locking hole to occur without creating a loose body.

In an embodiment projection 156 (e.g., a land) is a projection of material that is radially oriented with an upper and lower surface that may be parallel to each other. In an embodiment there is no taper, angulation, or threaded relief to the land (e.g., there is a 90 degree angle between wall 162 and surface 158). The land may increase along the short axis of the locking hole (aperture formed by projection 156) if the underside of the locking plate is curved. The land is comprised of a thickness 186 and length 185.

In an embodiment the thickness 186 is critical to the function of the locking mechanism and is between 0.254 mm and 5.588 mm which allows for the thread of the locking head to cut into the projection without critically deforming the projection and allowing the screw to pull through the projection. The land thickness 186 is consistent around the circumference of the aperture in an embodiment. In an embodiment thickness 186 varies. Such an embodiment may include, for example, steps to vary the thickness.

In an embodiment 176' is larger than diameter 164' by 1.0668 mm. The smaller the counterbore diameter is the less angulation the screw can be locked in because the screw will contact the top surface 174. In alternative embodiments the presence of a countersink at the top of the counterbore circumvents this consideration.

In an embodiment a critical feature is the depth 184 of the reliefs, which may or may not be equal for each of the reliefs. Typically, the reliefs will have a depth 184 into the projection 156 from 0.127 mm to 0.381 mm. In an embodiment depth 184 is 0.3048 mm. If the depth of the relief is too shallow, the locking will be compromised. Similarly, if the depth is too deep the land may subject to a critical force and the land will deform too much and shear from the locking plate.

In an embodiment diameter 164' is a critical feature. The diameter is less than the head diameter 106 by 7 percent but may range from 2 to 15 percent less. The diameter is critical to the design and allows for the optimal amount of interference that allows the screw to bite/wedge into the locking hole (hole defined by projection 156) to create a solid one-piece construct. In an embodiment, the aperture has a diameter of 4.0767 mm.

Figure 5A:
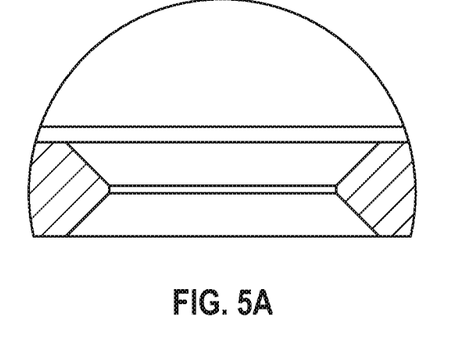
FIGS. 5A, 5B, 5C include cross-sectional views of differing embodiments of a bone plate.
Figure 5B:
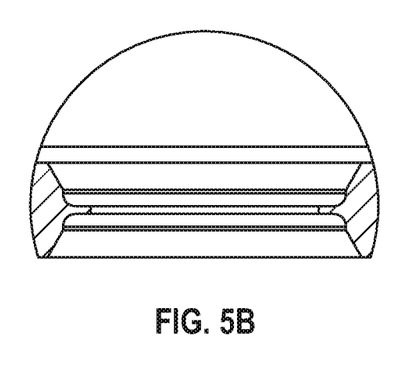
Figure 5C:
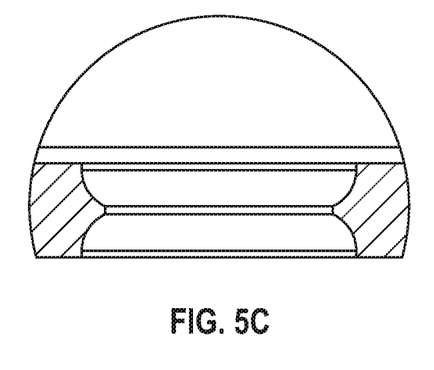

In an embodiment the upper counterbore depth has a sidewall 157 parallel with axis 153. However, a counterbore can be combined with other features such as a countersink (e.g., FIG. 5B). FIGS. 5A and 5C illustrate other alternative designs. In an embodiment the upper counterbore depth 172 is 0.889 mm.

In an embodiment a lower counterbore is present, but such a feature is optional. An embodiment includes a land with two parallel planes 160, 170. If a lower counterbore absent, the underside 175 may have a radius of curvature that is not parallel to the top surface 174 of the land. The presence of a lower counterbore or void aids in providing clearance of the locking screw at high angles. In an embodiment, the lower counter bore has a diameter 176" of 5.461 mm and a depth 173 of 0.127 mm.

A critical feature in some embodiments is the distance 185 of the projection of the locking hole land from the counterbore wall 157. This value may vary from 0.254 mm to 0.762 mm in various embodiments. The projection is critical to the locking mechanism because if the projection is too small, the angle that the screw and the ability to lock will be compromised. Additionally, if the projection is too long, the locking screw may translate through the locking hole.

In an embodiment, the angle of the upper counterbore wall 157 from the central axis 153 may be 0 degrees (parallel) but may range from 0 to 80 degrees in other embodiments. Further, the angle of the lower counterbore sidewall from axis 153 may be 0 degrees but may range from 0 to 80 degrees.

The following examples pertain to further embodiments.

Example 1

A bone fixation system comprising: a bone anchor; and a plate; wherein the bone anchor: (a)(i) includes a head and a body, the head being coupled to the body, (a)(ii) has a long axis, (a)(iii) the body has an outer diameter that is orthogonal to the long axis and the head has an outer diameter that is orthogonal to the long axis, and (a)(iv) the outer diameter of the head is greater than the outer diameter of the body; wherein: (b)(i) the plate includes an aperture, (b)(ii) the aperture includes a long axis that traverses the aperture but does not intersect the plate, (b)(iii) the aperture includes a first opening and a second opening, (b)(iv) the aperture includes a projection and the projection projects inwardly from a wall of the aperture and towards the long axis, (b)(v) the projection has a first surface and a second surface, and (b)(vi) at least a portion of the first surface is coplanar with a first plane, and (b)(vii) the first plane intersects the long axis at a first angle and the first angle is between 85 degrees and 95 degrees.

In an embodiment such a bone anchor may include what some call a "headless" screw. Such a screw may have varying pitch or lead (e.g., a larger pitch or lead near the distal end and a smaller pitch or lead near the proximal end). However, the screw may still taper to some extent, even if the taper near the proximal end is slight.

Example 2

The bone fixation system of example 1 wherein: the projection includes an inner wall that couples the first surface of the projection to the second surface of the projection; the inner wall of the projection has a first portion that is a first distance from the long axis, the first distance being orthogonal to the long axis; the inner wall of the projection has a second portion that is a second distance from the long axis, the second distance being orthogonal to the long axis; the second distance is greater than the first distance.

Example 3

The bone fixation system of example 2 wherein: the inner wall of the projection has a third portion that is a third distance from the long axis, the third distance being orthogonal to the long axis; the third distance is greater than the first distance.

Example 4

The bone fixation system of example 3 wherein: the third distance is greater than the second distance; the second distance is measured from a location of the second portion that is furthest from the long axis as compared to other locations of the second portion; the third distance is measured from a location of the third portion that is furthest from the long axis as compared to other locations of the third portion.

Example 5

The bone fixation system of example 3 wherein: the inner wall of the projection defines an inner perimeter of the projection; the inner wall of the projection has a fourth portion that is the first distance from the long axis; the first portion is between the second and third portions; the third portion is between the first and fourth portions.

Example 6

The bone fixation system of example 2 wherein the first plane is orthogonal to the long axis.

Example 7

The bone fixation system of example 1 wherein the first plane is orthogonal to the long axis.

Example 8

The bone fixation system of example 1 wherein at least a portion of the second surface is coplanar with a second plane, and (b)(viii) the second plane intersects the long axis at a second angle and the second angle is between 85 degrees and 95 degrees.

Example 9

The bone fixation system of example 8 wherein the second plane is orthogonal to the long axis.

Example 10

The bone fixation system of example 8 wherein the first plane is orthogonal to the long axis.

Example 11

The bone fixation system of example 1 wherein: the first surface is between the second surface and the first opening; the second surface is between the first surface and the second opening; the first surface is a first distance from the first opening, the first distance being parallel to the long axis; the second surface is a second distance from the second opening, the second distance being parallel to the long axis; the first distance is greater than the second distance.

Example 12

The bone fixation system of example 1 wherein: the plate includes no threads between the first and second openings; the first opening directly interfaces a first outer surface of the plate; the second opening directly interfaces a second outer surface of the plate; the first outer surface of the plate opposes the second outer surface of the plate.

Example 13

The bone fixation system of example 12 wherein: the first opening has a first maximum diameter that is orthogonal to the long axis; the second opening has a second maximum diameter that is orthogonal to the long axis; the second maximum diameter is greater than the first maximum diameter.

Example 14

The bone fixation system of example 13 wherein: the head of the bone anchor includes a third maximum diameter; the first maximum diameter is greater than the third maximum diameter; the projection forms a ring that circumnavigates an inner portion of the aperture; the ring has a minimum diameter; the minimum diameter of the ring is less than the third maximum diameter.

Example 15

The bone fixation system of example 1 wherein: at least a portion of the head of the bone anchor is included in a proximal-most fifth of the bone anchor; the portion of the head of the bone anchor includes threads.

Example 16

The bone fixation system of example 15 wherein: the body of the bone anchor includes threads; the threads of the body of the bone anchor have a first thread height; the threads of the portion of the head of the bone anchor have a second thread height; the second thread height is less than the first thread height.

Example 17

The bone fixation system of example 16 wherein: the threads of the body of the bone anchor have a first crest width; the threads of the portion of the head of the bone anchor have a second crest width; the second crest width is greater than the first crest width.

Example 18

The bone fixation system of example 1 wherein the projection forms a ring that circumnavigates an inner portion of the aperture.

Example 19

The bone fixation system of example 1 wherein: the head of the bone anchor has a circular cross-section, the cross-section being orthogonal to the long axis of the bone anchor; the outer diameter of the head is greater than the outer diameter of the body based on the bone anchor including a tapered portion; the tapered portion includes a thread root that tapers outwardly at an angle between 10 degrees and 25 degrees; the head of the bone anchor includes a maximum diameter taken orthogonal to the long axis of the bone screw; the projection forms a ring that circumnavigates an inner portion of the aperture, the ring including a minimum diameter; the maximum diameter of the head of the bone anchor is between 5 percent and 10 percent larger than the minimum diameter of the ring; at least a portion of the head of the bone anchor is included in a proximal-most fifth of the bone anchor, the portion of the head of the bone anchor including threads; the threads of the portion of the head of the bone anchor have a thread height, the thread height being between 0.0254 mm and 0.3048 mm; the threads of the portion of the head of the bone anchor have a crest width, the crest width being between 0.0508 mm and 0.3048 mm; the first surface is between the second surface and the first opening and the second surface is between the first surface and the second opening; the first surface is a first distance from the first opening, the first distance being parallel to the long axis and being between 0.254 mm and 1.27 mm; the projection includes an inner wall that couples the first surface of the projection to the second surface of the projection; the inner wall of the projection has a first portion that is a second distance from the long axis, the second distance being orthogonal to the long axis; the inner wall of the projection has a second portion that is a third distance from the long axis, the third distance being orthogonal to the long axis; the third distance is greater than the second distance and the third distance is between 0.508 mm and 1.016 mm; the third distance is greater than the second distance by a differential distance and the differential distance is between 0.127 mm and 0.381 mm; the first surface is a fourth distance from the second surface, the fourth distance being parallel to the long axis and being between 0.254 mm and 5.588 mm; the first portion of the projection projects inwardly from the wall of the aperture and towards the long axis by a fifth distance, the fifth distance being between 0.254 mm and 0.127 mm.

Example 19.5

The bone fixation system of example 19 wherein the threads of the portion of the head of the bone anchor include thread crests that taper outwardly at an angle between 10 degrees and 20 degrees.

Example 20

A bone fixation system comprising: a bone anchor with a tapered head, the head being threaded; and a plate that includes a void, the void including one of a counterbore or a countersink; wherein: no portion of the void is threaded; the void includes an inner wall; the inner wall includes reliefs along its perimeter;

Example 21

The bone fixation system of example 20 wherein: the void includes the counterbore; the counterbore includes a landing, the landing including a surface that is defined by a plane; the plane is orthogonal to a long axis of the void; the counterbore includes a sidewall, the sidewall extending parallel to the long axis of the void.

Example 22

The bone fixation system of example 20 wherein: the bone anchor includes a material; the plate includes the material; the bone anchor is monolithic; the plate is monolithic.

Example 23

The bone fixation system of example 21 wherein: the bone anchor and the reliefs are collectively configured such that threads of the bone anchor head deform the landing adjacent at least one of the reliefs when the bone anchor mates with the plate; the bone anchor and the reliefs are collectively configured to lock the bone anchor to the plate in response to the threads of the bone anchor head deforming the landing.

Example 24

The bone fixation system of example 23 wherein the plate includes no resilient members.

For example, some conventional techniques may use a wire (e.g., nickel-chrome alloy with shape memory) that moves laterally while a screw is being inserted and then snaps back medially and over the screw head to prevent screw backout. However, no such resilient member is included in an embodiment of the plate.

Example 25

A bone fixation kit comprising: a plate that includes a void, the void including one of a counterbore or a countersink; wherein: the plate includes no resilient members; no portion of the void is threaded; the void includes an inner wall; the inner wall includes reliefs along its perimeter; the reliefs are configured such that threads of a bone anchor head will deform the inner wall adjacent at least one of the reliefs when the bone anchor mates with the plate.

Example 26

The bone fixation kit of example 25 wherein: the void includes the counterbore; the counterbore includes a landing, the landing including a surface that is defined by a plane; the plane is orthogonal to a long axis of the void; the counterbore includes a sidewall, the sidewall extending parallel to the long axis of the void.

Example 27

The bone fixation kit of example 25 comprising the bone anchor.

Example 5a

The bone fixation system according to any of examples 3-4 wherein: the inner wall of the projection defines an inner perimeter of the projection; the inner wall of the projection has a fourth portion that is the first distance from the long axis; the first portion is between the second and third portions; the third portion is between the first and fourth portions.

Example 6a

The bone fixation system according to any of examples 1-5 wherein the first plane is orthogonal to the long axis.

Example 8a

The bone fixation system according to any of examples 1-6 wherein at least a portion of the second surface is coplanar with a second plane, and (b)(viii) the second plane intersects the long axis at a second angle and the second angle is between 85 degrees and 95 degrees.

Example 10a

The bone fixation system according to any of examples 1-9 wherein the first plane is orthogonal to the long axis.

Example 11a

The bone fixation system according to any of examples 1-10 wherein: the first surface is between the second surface and the first opening; the second surface is between the first surface and the second opening; the first surface is a first distance from the first opening, the first distance being parallel to the long axis; the second surface is a second distance from the second opening, the second distance being parallel to the long axis; the first distance is greater than the second distance.

Example 12a

The bone fixation system according to any of examples 1-11 wherein: the plate includes no threads between the first and second openings; the first opening directly interfaces a first outer surface of the plate; the second opening directly interfaces a second outer surface of the plate; the first outer surface of the plate opposes the second outer surface of the plate.

Example 15a

The bone fixation system according to any of examples 1-14 wherein: at least a portion of the head of the bone anchor is included in a proximal-most fifth of the bone anchor; the portion of the head of the bone anchor includes threads.

Example 18a

The bone fixation system according to any of examples 1-17 wherein the projection forms a ring that circumnavigates an inner portion of the aperture.

Example 19a

The bone fixation system according to any of examples 1-18 wherein: the head of the bone anchor has a circular cross-section, the cross-section being orthogonal to the long axis of the bone anchor; the outer diameter of the head is greater than the outer diameter of the body based on the bone anchor including a tapered portion; the tapered portion includes a thread root that tapers outwardly at an angle between 10 degrees and 20 degrees; the head of the bone anchor includes a maximum diameter taken orthogonal to the long axis of the bone screw; the projection forms a ring that circumnavigates an inner portion of the aperture, the ring including a minimum diameter; the maximum diameter of the head of the bone anchor is between 5 percent and 10 percent larger than the minimum diameter of the ring; at least a portion of the head of the bone anchor is included in a proximal-most fifth of the bone anchor, the portion of the head of the bone anchor including threads; the threads of the portion of the head of the bone anchor have a thread height, the thread height being between 0.0254 mm and 0.3048 mm; the threads of the portion of the head of the bone anchor have a crest width, the crest width being between 0.0508 mm and 0.3048 mm; the first surface is between the second surface and the first opening and the second surface is between the first surface and the second opening; the first surface is a first distance from the first opening, the first distance being parallel to the long axis and being between 0.254 mm and 1.27 mm; the projection includes an inner wall that couples the first surface of the projection to the second surface of the projection; the inner wall of the projection has a first portion that is a second distance from the long axis, the second distance being orthogonal to the long axis; the inner wall of the projection has a second portion that is a third distance from the long axis, the third distance being orthogonal to the long axis; the third distance is greater than the second distance and the third distance is between 0.508 mm and 1.016 mm; the third distance is greater than the second distance by a differential distance and the differential distance is between 0.127 mm and 0.381 mm; the first surface is a fourth distance from the second surface, the fourth distance being parallel to the long axis and being between 0.254 mm and 5.588 mm; the first portion of the projection projects inwardly from the wall of the aperture and towards the long axis by a fifth distance, the fifth distance being between 0.254 mm and 0.127 mm.

Example 22a

The bone fixation system according to any of examples 20-21 wherein: the bone anchor includes a material; the plate includes the material; the bone anchor is monolithic; the plate is monolithic.

As used herein, monolithic means formed of a single unit. For example, the plate may be formed by forging, machining of a block of material, additive manufacturing, and the like. Such a unit would not include welds or portions joined via adhesives.

Example 23a

The bone fixation system according to any of examples 20-22 wherein: the bone anchor and the reliefs are collectively configured such that threads of the bone anchor head deform the landing adjacent at least one of the reliefs when the bone anchor mates with the plate; the bone anchor and the reliefs are collectively configured to lock the bone anchor to the plate in response to the threads of the bone anchor head deforming the landing.

Example 24a

The bone fixation system according to any of examples 20-23 wherein the plate includes no resilient members.

Example 27a

The bone fixation kit according to any of examples 25-26 comprising the bone anchor.

Example 6a'

The bone fixation system according to any of examples 5a wherein the first plane is orthogonal to the long axis.

Example 8a'

The bone fixation system according to any of examples 5a-6a wherein at least a portion of the second surface is coplanar with a second plane, and (b)(viii) the second plane intersects the long axis at a second angle and the second angle is between 85 degrees and 95 degrees.

Example 10a'

The bone fixation system according to any of examples 5a, 6a, 8a wherein the first plane is orthogonal to the long axis.

Example 11a'

The bone fixation system according to any of examples 5a, 6a, 8a, 10a wherein: the first surface is between the second surface and the first opening; the second surface is between the first surface and the second opening; the first surface is a first distance from the first opening, the first distance being parallel to the long axis; the second surface is a second distance from the second opening, the second distance being parallel to the long axis; the first distance is greater than the second distance.

Example 12a'

The bone fixation system according to any of examples 5a, 6a, 8a, 10a, 11a wherein: the plate includes no threads between the first and second openings; the first opening directly interfaces a first outer surface of the plate; the second opening directly interfaces a second outer surface of the plate; the first outer surface of the plate opposes the second outer surface of the plate.

Example 15a'

The bone fixation system according to any of examples 5a, 6a, 8a, 10a, 11a, 14a wherein: at least a portion of the head of the bone anchor is included in a proximal-most fifth of the bone anchor; the portion of the head of the bone anchor includes threads.

Example 18a'

The bone fixation system according to any of examples 5a, 6a, 8a, 10a, 11a, 14a, 17a wherein the projection forms a ring that circumnavigates an inner portion of the aperture.

Example 19a'

The bone fixation system according to any of examples 5a, 6a, 8a, 10a, 11a, 14a, 17a, 18a wherein: the head of the bone anchor has a circular cross-section, the cross-section being orthogonal to the long axis of the bone anchor; the outer diameter of the head is greater than the outer diameter of the body based on the bone anchor including a tapered portion; the tapered portion includes a thread root that tapers outwardly at an angle between 10 degrees and 20 degrees; the head of the bone anchor includes a maximum diameter taken orthogonal to the long axis of the bone screw; the projection forms a ring that circumnavigates an inner portion of the aperture, the ring including a minimum diameter; the maximum diameter of the head of the bone anchor is between 5 percent and 10 percent larger than the minimum diameter of the ring; at least a portion of the head of the bone anchor is included in a proximal-most fifth of the bone anchor, the portion of the head of the bone anchor including threads; the threads of the portion of the head of the bone anchor have a thread height, the thread height being between 0.0254 mm and 0.3048 mm; the threads of the portion of the head of the bone anchor have a crest width, the crest width being between 0.0508 mm and 0.3048 mm; the first surface is between the second surface and the first opening and the second surface is between the first surface and the second opening; the first surface is a first distance from the first opening, the first distance being parallel to the long axis and being between 0.254 mm and 1.27 mm; the projection includes an inner wall that couples the first surface of the projection to the second surface of the projection; the inner wall of the projection has a first portion that is a second distance from the long axis, the second distance being orthogonal to the long axis; the inner wall of the projection has a second portion that is a third distance from the long axis, the third distance being orthogonal to the long axis; the third distance is greater than the second distance and the third distance is between 0.508 mm and 1.016 mm; the third distance is greater than the second distance by a differential distance and the differential distance is between 0.127 mm and 0.381 mm; the first surface is a fourth distance from the second surface, the fourth distance being parallel to the long axis and being between 0.254 mm and 5.588 mm; the first portion of the projection projects inwardly from the wall of the aperture and towards the long axis by a fifth distance, the fifth distance being between 0.254 mm and 0.127 mm.

Example 23a'

The bone fixation system according to any of examples 22a wherein: the bone anchor and the reliefs are collectively configured such that threads of the bone anchor head deform the landing adjacent at least one of the reliefs when the bone anchor mates with the plate; the bone anchor and the reliefs are collectively configured to lock the bone anchor to the plate in response to the threads of the bone anchor head deforming the landing.

Example 24a'

The bone fixation system according to any of examples 22a, 23a wherein the plate includes no resilient members.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first structure "on" a second structure is directly on and in immediate contact with the second structure unless such is specifically stated; there may be a third structure or other structure between the first structure and the second structure on the first structure. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A bone fixation system comprising:
a bone anchor with a tapered head, the head being threaded; and
a plate that includes a void and opposing outer surfaces, the void including one of a counterbore or a countersink and the outer surfaces including first and second openings into the void;
wherein: (a) no portion of the void is threaded; (b) the void includes an inner wall and the inner wall includes reliefs along its perimeter; (c) measured orthogonal to a long axis of the void, the second opening is wider than the first opening, and (d) measured parallel to the long axis, the reliefs are further from the first opening than the second opening.

2. The bone fixation system of claim 1 wherein:
the void includes the counterbore;
the counterbore includes a landing, the landing including a surface that is defined by a plane;
the plane is orthogonal to the long axis of the void;
the counterbore includes a sidewall, the sidewall extending parallel to the long axis of the void.

3. The bone fixation system of claim 1 wherein:
the bone anchor includes a material;
the plate includes the material;
the bone anchor is monolithic;
the plate is monolithic.

4. The bone fixation system of claim 1 wherein:
the bone anchor and the reliefs are collectively configured such that threads of the bone anchor head deform the landing adjacent at least one of the reliefs when the bone anchor mates with the plate;
the bone anchor and the reliefs are collectively configured to lock the bone anchor to the plate in response to the threads of the bone anchor head deforming the landing.

5. The bone fixation system of claim 4 wherein the plate includes no resilient members.

6. The bone fixation system of claim 1 wherein:
the long axis traverses the void but does not intersect the plate;
a plane, orthogonal to the long axis, intersects the first opening and one of the outer surfaces;
another plane, orthogonal to the long axis, intersects the second opening and another of the outer surfaces.

7. A bone fixation kit comprising:
a plate that includes a void and opposing outer surfaces, the void including one of a counterbore or a countersink and the outer surfaces including first and second openings into the void;
wherein:
the plate includes no resilient members;
no portion of the void is threaded;
the void includes an inner wall;
the inner wall includes reliefs along its perimeter;
the reliefs are configured such that threads of a bone anchor head will deform the inner wall adjacent at least one of the reliefs when the bone anchor mates with the plate;
measured orthogonal to a long axis of the void, the second opening is wider than the first opening, and
measured parallel to the long axis, the reliefs are further from the first opening than the second opening.

8. The bone fixation kit of claim 7 wherein:
the void includes the counterbore;
the counterbore includes a landing, the landing including a surface that is defined by a plane;
the plane is orthogonal to the long axis of the void;
the counterbore includes a sidewall, the sidewall extending parallel to the long axis of the void.

9. The bone fixation kit of claim 7 comprising the bone anchor.

10. A bone fixation system comprising:
a bone anchor; and
a plate;
wherein: (a)(i) the bone anchor includes a head and a body, the head being coupled to the body, (a)(ii) the bone anchor has a long axis, (a)(iii) the body has an outer diameter that is orthogonal to the long axis and the head has an outer diameter that is orthogonal to the long axis, and (a)(iv) the outer diameter of the head is greater than the outer diameter of the body;
wherein: (b)(i) the plate includes an aperture, (b)(ii) the aperture includes a long axis that traverses the aperture but does not intersect the plate, (b)(iii) the aperture includes a first opening and a second opening, (b)(iv) the aperture includes a projection and the projection projects inwardly from a wall of the aperture and towards the long axis, (b)(v) the projection has a first surface and a second surface, and (b)(vi) at least a portion of the first surface is coplanar with a first plane, and (b)(vii) the first plane intersects the long axis at a first angle and the first angle is between 85 degrees and 95 degrees;

wherein: (c)(i) the plate includes no threads between the first and second openings; (c)(ii) the first opening directly interfaces a first outer surface of the plate; (c)(iii) the second opening directly interfaces a second outer surface of the plate; and (c)(iv) the first outer surface of the plate opposes the second outer surface of the plate;

wherein: (d)(i) the first opening has a first maximum diameter that is orthogonal to the long axis; (d)(ii) the second opening has a second maximum diameter that is orthogonal to the long axis; (d)(iii) the second maximum diameter is greater than the first maximum diameter; and (d)(iv) the first opening is configured to receive the head of the bone anchor;

wherein the head of the bone anchor has a circular cross-section, the cross-section being orthogonal to the long axis of the bone anchor;

wherein the outer diameter of the head is greater than the outer diameter of the body based on the bone anchor including a tapered portion;

wherein the tapered portion includes a thread root that tapers outwardly at an angle between 10 degrees and 25 degrees;

wherein the head of the bone anchor includes a maximum diameter taken orthogonal to the long axis of the bone screw;

wherein the projection forms a ring that circumnavigates an inner portion of the aperture, the ring including a minimum diameter;

wherein the maximum diameter of the head of the bone anchor is between 5 percent and 10 percent larger than the minimum diameter of the ring;

wherein at least a portion of the head of the bone anchor is included in a proximal-most fifth of the bone anchor, the portion of the head of the bone anchor including threads;

wherein the threads of the portion of the head of the bone anchor have a thread height, the thread height being between 0.0254 mm and 0.3048 mm;

wherein the threads of the portion of the head of the bone anchor have a crest width, the crest width being between 0.0508 mm and 0.3048 mm;

wherein the first surface is between the second surface and the first opening and the second surface is between the first surface and the second opening;

wherein the first surface is a first distance from the first opening, the first distance being parallel to the long axis and being between 0.254 mm and 1.27 mm;

wherein the projection includes an inner wall that couples the first surface of the projection to the second surface of the projection;

wherein the inner wall of the projection has a first portion that is a second distance from the long axis, the second distance being orthogonal to the long axis;

wherein the inner wall of the projection has a second portion that is a third distance from the long axis, the third distance being orthogonal to the long axis;

wherein the third distance is greater than the second distance and the third distance is between 0.508 mm and 1.016 mm;

wherein the third distance is greater than the second distance by a differential distance and the differential distance is between 0.127 mm and 0.381 mm;

wherein the first surface is a fourth distance from the second surface, the fourth distance being parallel to the long axis and being between 0.254 mm and 5.588 mm;

wherein the first portion of the projection projects inwardly from the wall of the aperture and towards the long axis by a fifth distance, the fifth distance being between 0.254 mm and 0.127 mm.

11. The bone fixation system of claim 10 wherein:
the inner wall of the projection has a third portion that is a sixth distance from the long axis, the sixth distance being orthogonal to the long axis;
the sixth distance is greater than the second distance.

12. The bone fixation system of claim 11 wherein:
the sixth distance is greater than the third distance;
the third distance is measured from a location of the second portion that is furthest from the long axis as compared to other locations of the second portion;
the sixth distance is measured from a location of the third portion that is furthest from the long axis as compared to other locations of the third portion.

13. The bone fixation system of claim 11 wherein:
the inner wall of the projection defines an inner perimeter of the projection;
the inner wall of the projection has a fourth portion that is the second distance from the long axis;
the first portion is between the second and third portions;
the third portion is between the first and fourth portions.

14. The bone fixation system of claim 13 wherein the first plane is orthogonal to the long axis.

15. The bone fixation system of claim 10 wherein the first plane is orthogonal to the long axis.

16. The bone fixation system of claim 10 wherein at least a portion of the second surface is coplanar with a second plane, and (b)(viii) the second plane intersects the long axis at a second angle and the second angle is between 85 degrees and 95 degrees.

17. The bone fixation system of claim 16 wherein the second plane is orthogonal to the long axis.

18. The bone fixation system of claim 16 wherein the first plane is orthogonal to the long axis.

19. The bone fixation system of claim 10 wherein:
the second surface is an additional distance from the second opening, the additional distance being parallel to the long axis;
the first distance is greater than the additional distance.

20. The bone fixation system of claim 10 wherein:
the first maximum diameter is greater than the maximum diameter of the head of the bone anchor;
the minimum diameter of the ring is less than the maximum diameter of the head of the bone anchor.

21. The bone fixation system of claim 10 wherein:
the body of the bone anchor includes threads;
the threads of the body of the bone anchor have a first thread height;
the thread height of the threads of the portion of the bone anchor is less than the first thread height.

22. The bone fixation system of claim 21 wherein:
the threads of the body of the bone anchor have a first crest width;
the crest width of the threads of the portion of the head of the bone anchor is greater than the first crest width.

23. The bone fixation system of claim 10 wherein there is no additional projection between the first plane and second outer surface.

* * * * *